United States Patent

Delobeau et al.

[11] Patent Number: 5,846,794
[45] Date of Patent: Dec. 8, 1998

[54] PROCESS FOR THE PREPARATION OF D-ARABITOL

[75] Inventors: Didier Delobeau; Didier Moine, both of Merville, France

[73] Assignee: Roquette Freres, France

[21] Appl. No.: 863,579

[22] Filed: May 27, 1997

[30] Foreign Application Priority Data

May 29, 1996 [FR] France .................................. 96 06599

[51] Int. Cl.⁶ ............................... C12P 7/18; C12P 19/02; C07C 31/18
[52] U.S. Cl. ........................... 435/158; 435/105; 435/155; 568/852; 568/863; 526/1.11; 526/124
[58] Field of Search ................................... 536/1.11, 124; 568/852, 863; 435/105, 158, 155

[56] References Cited

U.S. PATENT DOCUMENTS

| | | |
|---|---|---|
| 4,156,076 | 5/1979 | Dehlgren . |
| 4,259,443 | 3/1981 | Danehy . |
| 4,845,208 | 7/1989 | Fuertes et al. . |
| 5,096,820 | 3/1992 | Leleu et al. . |
| 5,132,452 | 7/1992 | Deller et al. . |
| 5,238,826 | 8/1993 | Leleu et al. . |

FOREIGN PATENT DOCUMENTS

| | | |
|---|---|---|
| 0 142 725 | 5/1985 | European Pat. Off. . |
| 2453214 | 10/1980 | France . |
| WO 93/19030 | 9/1993 | WIPO . |

OTHER PUBLICATIONS

Fletcher, H.G., and Coll., Journal of the American Chemical Society, 1950, vol. 72, p 4546.
Patent Abstracts of Japan, vol. 006, No. 127 (C–113), Jul. 13, 1982.
Journal of the American Chemical Society, vol. 56, No. 197, Jul. 5, 1934.
Berichte der Deutschen Chemischen Gesellschaft, vol. 32, Feb. 27, 1989.

*Primary Examiner*—Francisco C. Prats
*Attorney, Agent, or Firm*—Henderson & Sturm

[57] ABSTRACT

A process for the preparation of D-arabitol, characterised in that it comprises the following stages:
  hydrolysis of a lactose solution,
  oxidation of the mixture of glucose and galactose thus obtained to a mixture of gluconic and galactonic acids,
  decarboxylation of this mixture of gluconic and galactonic acids to a mixture of D-arabinose and D-lyxose,
  catalytic hydrogenation of this mixture of D-arabinose and D-lyxose to D-arabitol.

9 Claims, No Drawings

PROCESS FOR THE PREPARATION OF D-ARABITOL

The object of the present invention is a process for the preparation of D-arabitol from mixtures of glucose and galactose.

Advantageously, the present invention relates to a process for the preparation of D-arabitol from lactose hydrolysates.

D-arabitol is an important synthesis intermediate for the production of xylitol. Xylitol is an acariogenic substitute for sucrose and is, as such, experiencing growing success, particularly in sugar-free confectionery.

Processes by which it is possible to obtain D-arabitol and to convert D-arabitol to xylitol are described, for example, in American patents U.S. Pat. No. 5.096.820 and U.S. Pat. No. 5.238.826, of which the Applicant is the assignee.

Said processes consist in oxidising D-arabitol to D-xylulose by microbial means, isomerising said D-xylulose to D-xylose, then hydrogenating catalytically the D-xylose to xylitol.

The raw material by which D-arabitol may be obtained in this case is glucose which is either fermented directly to D-arabitol or oxidised to gluconic acid which is itself decarboxylated to D-arabinose which is finally hydrogenated catalytically to D-arabitol.

Such processes have the disadvantage of using only glucose as the raw material.

Another process by which it is possible to obtain D-arabitol and then to convert the D-arabitol to xylitol is also described in the international patent application 93/19030.

It consists in isomerising a solution of D-arabitol at high temperature, under an elevated hydrogen pressure and under the action of a ruthenium-based catalyst. About 20% of the arabitol is isomerised in this way to xylitol.

Xylitol is then extracted from this mixture by chromatography and the D-arabitol that has not reacted undergoes isomerisation once more.

The raw material by which D-arabitol may be obtained in this case is either glucose which is degraded oxidatively to D-arabinonic acid which is hydrogenated catalytically to D-arabitol after lactonisation of the acid, or galactose which is degraded oxidatively to D-lyxonic acid which is hydrogenated catalytically to D-arabitol, also after lactonisation of the acid.

Such a process would therefore have the advantage of being able to use lactose hydrolysates as the raw material for the production of D-arabitol but suffer the enormous disadvantage that the catalytic hydrogenation of D-arabinonic acid or D-lyxonic acid to D-arabitol is extremely difficult to carry out and the yields are very poor.

The reason is, as indicated in this patent application, that the salts of said pentonic acids can not be hydrogenated and that they first have to be converted to esters or lactones.

However, even using very expensive ruthenium catalysts, the yields of the hydrogenation of lactones are very poor. Similarly, better yields cannot be obtained by using more conventional catalysts based on RANEY nickel, even if they are used weight for weight with respect to the D-arabino-1-4-lactone undergoing hydrogenation.

Another process for obtaining D-arabitol from lactose is described in American patent U.S. Pat. No. 4.156.076.

The process described in this patent consists in oxidising lactose to lactobionic acid, then hydrolysing this acid to a mixture of galactose and gluconic acid. The sugar and the acid are then separated and only the separated gluconic acid is used to obtain D-arabitol by decarboxylation to D-arabinose then hydrogenation. Half of the raw material is thus lost in the form of galactose or has to be made use of in another way.

All these processes for obtaining D-arabitol are therefore unsatisfactory because, in the case of the first processes mentioned, they suffer the disadvantage of using glucose, a relatively expensive raw material, and in the case of the second, they suffer from poor reaction yields which have a very adverse effect on the extremely attractive price of lactose, associated with its great availability and the difficulty of enhancing its value in another form.

The object of the present invention is, therefore, to provide a process by which it is possible to overcome the above-mentioned disadvantages and to find an outlet that will enhance the value of lactose by converting it to D-arabitol.

A process has now been found for the preparation of D-arabitol, this being the object of the present invention, which is characterised in that it comprises the following stages:

hydrolysis of a lactose solution, oxidation of the mixture of glucose and galactose thus obtained to a mixture of gluconic and galactonic acids, decarboxylation of this mixture of gluconic and galactonic acids to a mixture of D-arabinose and D-lyxose, catalytic hydrogenation of this mixture of Darabinose and D-lyxose to D-arabitol.

Although lactose is the preferred raw material in the process according to the invention, mixtures of glucose and lactose or of galactose and lactose may also be used in this process. Similarly, certain vegetable hydrolysates of wood or straw, composed almost exclusively of glucose and galactose, may also be used.

The process of the invention comprises, therefore, a first operation involving hydrolysis of a lactose solution, which makes it possible to separate this molecule into its two constituents and to obtain an equimolar mixture of free glucose and galactose.

The hemiacetal function of galactose which used to be part of an -oside bond with glucose is liberated by this hydrolysis and hence becomes available for oxidation, in the same way as the hemiacetal function of glucose which was already free in the lactose molecule.

Without separation of the components of the intermediate hydrolysate, the process continues with the stage of controlled oxidation of glucose and galactose, which oxidation converts the hemiacetal functions of glucose and galactose to carboxyl functions. A mixture containing gluconic and galactonic acids is obtained in this way.

Still without separating the acids obtained, the process of the invention is continued with the stage of decarboxylation of these acids.

By excising the carboxyl function and reestablishing a hemiacetal function on the thus shortened carbon skeleton of the acids, a mixture of D-arabinose and D-lyxose is obtained.

Finally, by catalytic hydrogenation of this mixture of D-arabinose and D-lyxose, and still without separating the two principal components of the mixture, D-arabitol is obtained in the practically pure state since D-lyxitol is a synonym of D-arabitol.

The process of the invention is particularly attractive because it makes it possible to obtain D-arabitol with a very good reaction yield. Indeed, all the lactose molecule is used without it ever being necessary to carry out any separation whatsoever of the synthesis intermediates.

Finally, another advantage of the invention, and an important one at that, is that the catalytic hydrogenation stage that it comprises is carried out on hemiacetal functions which are very easy to reduce to primary alcohols with yields and selectivity around 100% and with the aid of cheap RANEY nickel catalysts used in truly catalytic quantities.

In the process of the invention it is not, therefore, necessary to have to deal with expensive ruthenium catalysts which, moreover, are poisoned by the slightest trace of formic acid, any more than it is necessary to have to lactonise the acids that form as intermediates or to use toxic and dangerous solvents as indicated in the international patent application WO 93/19030 already cited.

The process of the invention thus makes it possible to enhance the value of all the lactose molecule at the best cost in an efficient process for the preparation of D-arabitol.

According to the process of the invention, the step involving the hydrolysis of lactose is carried out by chemical means or with enzymes.

If chemical means are used, it is preferable to use strong acids which do not oxidise under the conditions of their use. Hydrochloric or sulphuric acids are thus preferred whereas nitric acid must be avoided as it leads to more complex oxidation reactions of lactose. The quantities of strong acid to be used vary but remain catalytic. They depend on the hydrolysis time, the temperature of this hydrolysis and the lactose concentration of the solution to be hydrolysed.

Hydrolysis of lactose with enzymes may be carried out with the aid of beta-galactosidase. The temperatures used in the case of hydrolysis with enzymes are lower than those used when the hydrolysis of lactose is carried out by chemical means. It may therefore be necessary to use lower lactose concentrations in order to prevent any untimely crystallisation of this sugar.

A particularly suitable enzyme is LACTOZYM® beta-galactosidase sold by NOVO.

Whether hydrolysis is carried out by chemical means or with enzymes, it may be conducted batchwise or continuously, but in all cases it will be preferable to adjust the various parameters: time, concentration of the catalyst or enzyme, temperature, lactose concentration, in order to obtain a rate of lactose hydrolysis at least greater than 90% and preferably greater than 95%.

Such adjustments to the hydrolysis conditions are perfectly within the scope of the man skilled in the art who will be able to measure the rate of hydrolysis in a simple manner by determining the reducing ends that appear according to the BERTRAND method, for example, to cite only this method.

According to the process of the invention, the sugars obtained are not isolated and the next stage follows on directly, namely the oxidation of the mixture of glucose and galactose that form to a mixture of gluconic and galactonic acids.

According to the process of the invention, this oxidation stage may be carried out either by chemical means or by microbiological means.

The preferred chemical means in the process of the invention consists in oxidising, with air or oxygen in an alkaline medium and using palladium catalysts, the mixture of glucose and galactose obtained in the preceding stage.

A particularly preferred process is that which was described in the American patent U.S. Pat. No. 4.845.208 of which the Applicant is also the assignee, and which consists in using, as oxidation catalyst, palladium fixed on activated carbon and doped with bismuth.

It is also possible to envisage, in the process of the invention, oxidising the mixtures of glucose and galactose by electrolytic means or with the aid of hypobromite.

If the process described in the American patent U.S. Pat. No. 4.845.208 is used, it is preferable to operate with a sugar concentration between 10 and 40%, at a temperature between 25° and 60° C. with a quantity of palladium expressed in terms of metal of between 0.01% and 0.4% of the weight of the sugars. Under conditions where the oxygen input is not limiting, the oxidation of the mixture of glucose and galactose is complete in about 30 minutes to 5 hours.

The preferred alkaline agent within the context of the present invention is calcium carbonate or hydroxide. It is used to maintain a constant pH during the oxidation reaction, preferably between 8.0 and 10.0.

It is also possible to carry out the oxidation of the mixture of glucose and galactose by microbial means. In this case, small quantities of mineral salts and nutrient elements are added to the aqueous solutions of the lactose hydrolysate, said mineral salts and nutrient elements being added conveniently in the form of maize maceration liquor or yeast extract, for example.

After sterilisation of the culture medium thus obtained, the latter is seeded with a bacterial culture of a microorganism capable of oxidising glucose to gluconic acid and galactose to galactonic acid at the same time.

Microorganisms such as gluconobacter oxydans ATCC 19357 or ATCC 23773 are perfectly capable of oxidising these two sugars to the corresponding aldonic acids.

If these microorganisms are used, it is preferable to operate at sugar concentrations between 100 and 250 grams per liter and at a temperature of 25° to 35° C.

Under conditions where the oxygen input to the culture must is not a limiting factor, oxidation of the mixture of glucose and galactose is complete in about 15 to 30 hours.

In order to ensure that the bacterial oxidation takes place under satisfactory conditions, it is important to keep the pH at a value between 4.0 and 7.0. The preferred alkaline agent within the context of the present invention is also calcium carbonate or hydroxide.

Whether the oxidation of the lactose hydrolysate is carried out by chemical or microbial means, it is preferable to continue it until the quasi-disappearance of the reducing sugars and, in particular, until said reducing sugars represent less than 10% and even more preferably less than 5% of the dry matter undergoing oxidation.

At the end of this oxidation stage, the reaction media are filtered at a temperature sufficient to keep in solution the calcium salts of gluconic and galactonic acids in order to remove either the catalyst or the microorganisms.

To the Applicant's knowledge, such a stage involving the simultaneous oxidation of a mixture of galactose and glucose has never been described.

According to the process of the invention, the calcium salts of gluconic and galactonic acids thus obtained are not separated and the decarboxylation stage of these acids in this mixture follows on directly.

Although this decarboxylation stage may be carried out with the aid of hypochlorous acid, the process of the invention prefers to use the RUFF method which uses hydrogen peroxide.

To the Applicant's knowledge, such a decarboxylation stage, although described already, both for calcium gluconate and for calcium galactonate (FLETCHER H. G. and Coll. Journal of the American Chemical Society, 1950, Vol. 72. P. 4546) has never been described, however, for a mixture of these two salts.

The reason why the process of the invention is best carried out with the use of calcium salts of gluconic and galactonic acids and the RUFF process is that this decarboxylation stage of these hexonic acids leading to the corresponding pentoses thus leads to the very sparingly soluble calcium carbonate. It is therefore possible to lower considerably the mineral content of the resulting solution of pentoses by simple filtration of calcium carbonate.

The use of salts other than calcium salts is theoretically possible but proves to be considerably more expensive and less practical.

Similarly, the use of sodium hypochlorite instead of hydrogen peroxide used in the RUFF process would also greatly increase this mineral content.

According to a preferred mode of the process of the invention, the decarboxylation stage is therefore carried out on a solution of the calcium salts of gluconic and galactonic acids.

It is preferable to operate on solutions containing 100 to 400 grams per liter and preferably 200 to 300 grams per liter of anhydrous calcium hexonates and at a temperature of about 30° to 50° C.

This decarboxylation reaction is catalysed by ferric ions. In the process of the invention, it is preferable to add to the solution of calcium hexonates, ferric sulphate in a quantity of 1 to 5% of anhydrous ferric sulphate with respect to the weight of anhydrous hexonates. These ferric ions may, however, be introduced in another form.

The hydrogen peroxide is then added slowly with stirring, preferably in the form of hydrogen peroxide in a concentration of 30% in a quantity of about 120 to 140 milliliters per 100 grams of anhydrous hexonates.

The addition of hydrogen peroxide is carried out at a flow rate such that the temperature of the reaction medium does not rise above 50° C. The reaction is generally completed in 2 to 8 hours and its end is marked by the appearance of a purple colour.

The abundant precipitate of calcium carbonate which forms is filtered, preferably after the reaction medium has been allowed to cool. This reaction medium is then demineralised over a set of ion exchange resins composed of a strong cationic resin and a weak anionic resin, to which resins may be added a weak cationic resin and a strong anionic resin and/or a mixed bed of strong cationic and anionic resins.

The mineral content of the filtered reaction media may also be lowered by methods of ion exclusion chromatography over loaded cationic resins in the form of calcium before proceeding to the full demineralisation stage carried out with the above-mentioned resins.

After these purification treatments which may also comprise a decolorising step with the aid of vegetable charcoal, a colourless solution containing quasi-exclusively D-arabinose and D-lyxose is obtained.

The last stage of the process according to the invention consists in hydrogenating catalytically this solution of D-arabinose and D-lyxose without separating these two sugars from it.

As mentioned further above, such a hydrogenation focusing on hemiacetal functions is extremely easy to carry out. This is another of the major advantages of the process of the invention with respect to the process set out in the international patent application WO 93/19030 where hydrogenation focuses on esterified carboxyl functions of D-arabinonic and D-lyxonic acids.

To the Applicant's knowledge, such a hydrogenation of a largely equimolar mixture of D-arabinose and D-lyxose is also new.

The hydrogenation of such a mixture of sugars is carried out, however, in conformity with the rules of the art which lead, for example, to the production of sorbitol from glucose.

Ruthenium-based catalysts may be used just as easily as RANEY nickel catalysts for this stage.

It is preferable, however, to use RANEY nickel catalysts which are less expensive.

In practice, the catalyst is used in a quantity of 1 to 10% by weight with respect to the dry matter of sugar undergoing hydrogenation. Hydrogenation is carried out preferably on syrups, the dry matter content of which is between 15 and 50%, in practice around 30 to 45%, under a hydrogen pressure between 20 and 200 bars. It may be carried out continuously or batchwise.

If a batchwise procedure is adopted, the hydrogen pressure used is generally between 30 and 60 bars and the temperature at which hydrogenation takes place is between 100° and 150° C. It is also important to maintain the pH of the hydrogenation medium by adding soda or sodium carbonate, for example, but without exceeding a pH of 9.0. This method of operating makes it possible to avoid the appearance of other pentitols such as xylitol or ribitol which may appear following alkaline isomerisation of D-lyxose or D-arabinose. The reaction is stopped when the reducing sugar content of the reaction medium has become less than 1%, preferably less than 0.5%.

After the reaction medium has been cooled, the catalyst is removed by filtration and the syrup of D-arabitol thus obtained is demineralised over cationic and anionic resins.

At this stage, the syrups contain at least 90% of D-arabitol, and it is easy to remove this from them by crystallisation after concentrating and cooling the solutions.

However, the purity of the D-arabitol solutions obtained by the process of the invention is such that purification is not generally necessary if the intention is to continue the conversion of D-arabitol to xylitol by the processes described in the American patents U.S. Pat. No. 5.096.820 or U.S. Pat. No. 5.238.826 or in the international patent application 93/19030.

The process of the present invention makes it possible, therefore, due to the particular combination of steps that it claims, known in their principle but never described in this linked sequence with the mixtures of sugars or aldonic acids concerned, to enhance the value of the lactose easily and economically by converting it to D-arabitol.

Given that no synthesis intermediate needs to be isolated in the process of this invention, D-arabitol is obtained with an excellent yield, around 50% of the lactose used.

The invention will be better understood by means of the example that follows, the sole purpose of which is to better illustrate the invention without wishing to reduce it to the embodiment described therein.

EXAMPLE

1/Hydrolysis of Lactose

Crystalline lactose in its commercial form of monohydrate crystals is dissolved in water to a dry=matter content of 15%.

This lactose solution is brought to a temperature of 40° C. and its pH is adjusted to 6.5.

12,000 LAU units of beta-galactosidase LACTOZYM® 3000L sold by NOVO NORDISK DANEMARK per hundred grams of dry matter of lactose are then added, which represents 4 ml of enzyme and hydrolysis is allowed to continue for 8 hours.

The rate of hydrolysis of lactose is then 95%.

The solution is then brought to boiling in order to denature the enzyme, then it is purified by decolorising and demineralisation.

2/ Oxidation to Gluconic and Galactonic Acids

A catalyst is prepared, consisting of activated carbon on which has been deposited successively palladium then bismuth in a quantity of 35% of bismuth with respect to the palladium, as indicated in example 4 of the American patent U.S. Pat. No. 4.845.208, the disclosures of which are incorporated in the present description by this reference.

Oxidation of the lactose hydrolysate is then carried out, the dry matter content of which has been reduced to 12% as a result of the dilutions brought about by its purification.

To this end, operations are carried out in an aerated, stirred tank thermostated to 35° C., fitted with a pH measuring sensor, with the aid of 3% of catalyst obtained as indicated with respect to the dry matter of lactose hydrolysate.

Throughout the reaction which takes place in 3h30, the pH of the reaction medium is kept at a value between 8.5 and 9.1 by the gradual addition of milk of lime.

At the end of the reaction which is reflected in a halt in the consumption of lime, the catalyst is filtered. The reducing sugar content of this reaction medium is 1.5%.

3/ Decarboxylation to D-arabinose and D-lyxose

A solution of ferric sulphate is added to the filtrate of the calcium salts of gluconic and galactonic acids thus obtained so as to obtain a concentration of 3% of anhydrous ferric sulphate with respect to the dry matter of calcium hexonates used.

This solution is stirred and thermostated to 40° C. then hydrogen peroxide with a concentration of 30% is added slowly until a persistent brown-purple colour of the reaction mixture is obtained. This addition of hydrogen peroxide was carried out in 6 hours and 130 milliliters of hydrogen peroxide had to be added per 100 grams of calcium hexonates used.

After this reaction mixture has cooled for several hours, the calcium carbonate is filtered then this filtrate is demineralised over a strong cationic resin regenerated in the hydrogen form then a weak anionic resin regenerated in the hydroxyl form.

A virtually colourless solution of D-arabinose and D-lyxose is thus obtained which is concentrated to a dry matter content of 40%.

4/ Hydrogenation to D-arabitol

This syrup of pentoses to which 5% of RANEY nickel catalyst has been added is introduced into a stirred thermostated reactor which is then put under a hydrogen pressure of 50 bars and heated to 120° C.

The pH during this hydrogenation is kept at around neutrality with the aid of a solution of sodium carbonate. After 5 hours, the reducing sugar content of the reaction medium has become equal to 0.15% and the reactor is then cooled.

The catalyst is filtered, then the hydrogenated syrup is demineralised over strong cationic and anionic resins.

A colourless syrup containing 92% of D-arabitol is obtained.

We claim:

1. A process for the preparation of D-arabitol, wherein it comprises the following stages:

hydrolysis of a lactose solution, oxidation of the mixture of glucose and galactose thus obtained to a mixture of gluconic and galactonic acids, decarboxylation of this mixture of gluconic and galactonic acids to a mixture of D-arabinose and D-lyxose, catalytic hydrogenation of this mixture of D-arabinose and D-lyxose to D-arabitol.

2. A process for the preparation of D-arabitol according to claim 1, wherein the hydrolysis of the lactose solution is carried out by chemical means.

3. A process for the preparation of D-arabitol according to claim 1, wherein the hydrolysis of the lactose solution is carried out with enzymes.

4. A process for the preparation of D-arabitol according to claim 1, wherein the oxidation of the mixture of glucose and galactose is carried out in the presence of air or oxygen, in an alkaline medium and in the presence of palladium catalysts.

5. A process for the preparation of D-arabitol according to claim 1, wherein the oxidation of the mixture of glucose and galactose is carried out by microbial means using microorganisms.

6. A process for the production of D-arabitol according to claim 1, wherein the gluconic and galactonic acids are in the form of calcium salts.

7. A process for the production of D-arabitol according to claim 1, wherein the decarboxylation of the mixture of gluconic and galactonic acids is carried out using hydrogen peroxide.

8. A process for the production of D-arabitol according to claim 1, wherein the catalytic hydrogenation of the mixture of D-arabinose and D-lyxose is carried out using RANEY nickel.

9. A process for the preparation of D-arabitol according to claim 5, wherein said microorganisms comprise Gluconobacter oxydans.

* * * * *